United States Patent [19]
Kennedy et al.

[11] Patent Number: 5,634,711
[45] Date of Patent: Jun. 3, 1997

[54] PORTABLE LIGHT EMITTING APPARATUS WITH A SEMICONDUCTOR EMITTER ARRAY

[76] Inventors: John Kennedy, 11 Mollison Court, Guelph, Ontario, Canada, N1C 1A7; Roy Kayser, #307-2645 Jane Street, Toronto, Ontario, Canada, M3O 2J3

[21] Appl. No.: 305,514

[22] Filed: Sep. 13, 1994

Related U.S. Application Data

[63] Continuation-in-part of Ser. No. 119,571, Sep. 13, 1993, Pat. No. 5,420,768.

[51] Int. Cl.⁶ .................................................. B25B 33/00
[52] U.S. Cl. ..................... 362/119; 362/109; 362/800; 362/32; 362/294; 362/231; 433/29; 315/224
[58] Field of Search ........................... 433/29, 80, 215, 433/229; 128/303.1; 362/800, 183, 119, 109, 234, 184, 202, 294, 373, 32, 230, 231; 315/224, 127, 225, 119, 128; 363/21, 97, 55, 56; 320/13, 2

[56] References Cited

U.S. PATENT DOCUMENTS

| | | |
|---|---|---|
| 3,638,013 | 1/1972 | Keller . |
| 4,184,196 | 1/1980 | Moret et al. ........................ 362/138 |
| 4,230,453 | 10/1980 | Reimers . |
| 4,385,344 | 5/1983 | Gonser ................................ 362/32 |
| 4,398,885 | 8/1983 | Loge et al. . |
| 4,666,406 | 5/1987 | Kanca, III ......................... 433/229 |
| 4,729,076 | 3/1988 | Masami et al. ................... 362/235 |
| 4,810,194 | 3/1989 | Snedden ............................. 433/91 |
| 4,826,431 | 5/1989 | Fujimara et al. ................. 433/29 |
| 4,846,546 | 7/1989 | Cuda .................................. 385/116 |
| 4,888,489 | 12/1989 | Bryan . |
| 4,963,798 | 10/1990 | McDermott ..................... 362/800 X |
| 5,003,434 | 3/1991 | Gonser et al. . |
| 5,007,837 | 4/1991 | Werly . |
| 5,147,204 | 9/1992 | Patten et al. . |
| 5,150,016 | 9/1992 | Sawase ............................. 315/294 |
| 5,161,879 | 11/1992 | McDermott ..................... 362/800 X |
| 5,201,655 | 4/1993 | Friedman . |
| 5,233,283 | 8/1993 | Kennedy ........................... 320/13 |
| 5,290,169 | 3/1994 | Friedman ......................... 433/29 |

FOREIGN PATENT DOCUMENTS

| | | |
|---|---|---|
| 2212010 | 7/1989 | United Kingdom . |
| 93/09847 | 5/1993 | WIPO . |

OTHER PUBLICATIONS

Paper entitled "Miniaturized Tir Lenses for Light Emitting Diodes" by TIR Technologies, Inc., 1992.

*Primary Examiner*—Ira S. Lazarus
*Assistant Examiner*—Thomas M. Sember
*Attorney, Agent, or Firm*—Bereskin & Parr

[57] ABSTRACT

A hand-held portable light emitting device is suitable for medical and industrial photocuring and phototherapy applications. The hand-held portable light emitting device has: (a) a portable housing having a front end and a rear end; (b) a semiconducting light emitter having a matrix of a plurality of light emitting diodes mounted at the front end of the housing to emit light energy suitable for initiating a photoreaction; (c) a power supply connected to the light emitter to provide the electrical power for energizing the diodes to emit the light energy; (d) a controller connected to the light emitter and the power supply, to vary the level of the light energy; (e) a mount at the front end of the housing; and (f) an optical assembly mounted to the mount, to direct the light energy generated from the diodes to a photoreaction site near the optical assembly.

31 Claims, 5 Drawing Sheets

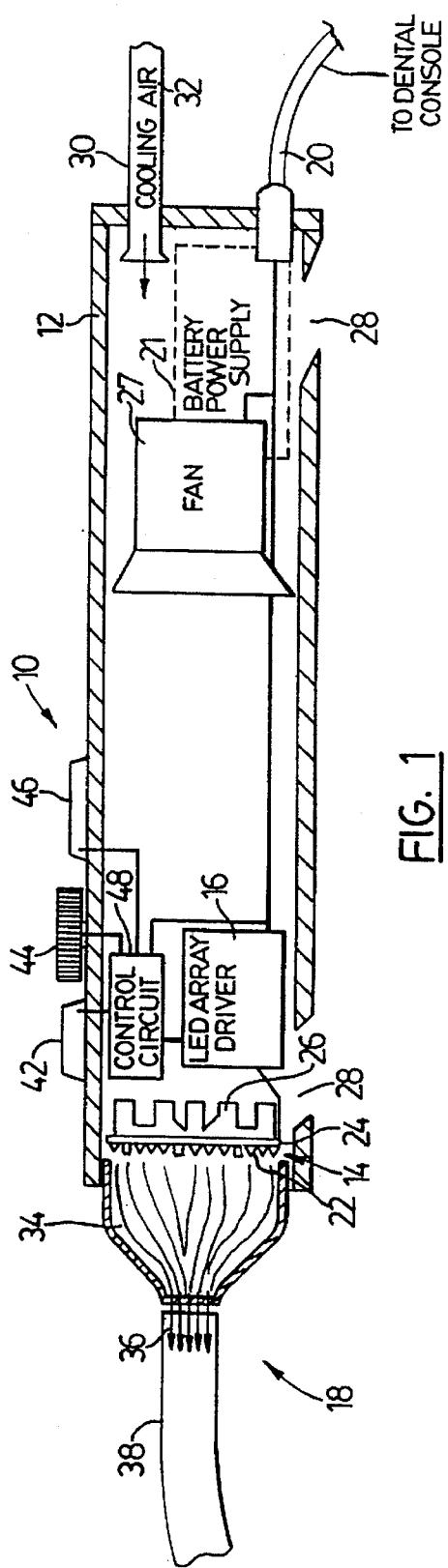

PORTABLE LIGHT EMITTING APPARATUS WITH A SEMICONDUCTOR EMITTER ARRAY

This application is a continuation-in-part of my application Ser. No. 08/119,571 filed Sep. 13, 1993, now U.S. Pat. No. 5,420,768, and entitled A Portable LED Photocuring Device.

FIELD OF THE INVENTION

This invention relates to light emitting devices, and more particularly relates to a portable or handheld light-emitting device which has particular, though by no means exclusive application, to non-thermal dental and industrial photocuring applications and medical phototherapy applications.

BACKGROUND OF THE INVENTION

In the art, there are numerous substances which are sensitive to light energy. The substances of interest generally fall into two classes. The first class comprises substances which undergo polymerization in response to applied light energy. The second class comprises light activated drugs which includes those drugs that produce a "singlet oxidation mechanism" in response to applied light energy. The second class of substances can be found in "photodynamic therapy" or "phototherapy" applications, while the first class of photo-sensitive substances are typically found in UV and visible light polymerization and photochemical curing of adhesives.

While there are known photochemical curing systems, these systems are designed as "bench-top" devices which tend to be bulky and therefore unsuitable for handheld applications. There are also known handheld devices. These devices also tend to be bulky and utilize quartz halogen light sources which produce considerable heat. Furthermore, the quart halogen light sources produce a broadband light output which has to be filtered to produce a selected spectral output. In many applications, for example, dental and medical, it is desirable to have a handheld or portable unit which produces a selected output and which can be easily manipulated in proximity to the patient.

The amount of light required depends on the application. For example, in a dental application, light dosage values in the range of up to 400 mW/cm$^2$ are typically required. On the other hand, a medical application, such as photodynamic therapy of psoriasis and basal cells, requires a much lower dosage typically in the range of to 100 mW/cm$^2$. Thus, it is desirable to have a portable device which can produce a range of light dosage output from low to high power values.

While known photochemical curing systems provide the capability to adjust the exposure time, they do not monitor the ongoing degradation of the intensity level produced by the light source. Thus, the performance of such a prior art system will steadily degrade over time unless the intensity level is manually measured and the exposure time adjusted accordingly. Therefore, it is also desirable to have the capability to monitor the intensity output for degradation in the light source.

Furthermore, in some applications, it may be desirable to increase the intensity level instead of the exposure time in order to provide an light energy output which is optimum for the curing application. Moreover, the light energy output level should be maintained at a consistent level over the operable life of the light source.

BRIEF SUMMARY OF THE INVENTION

The present invention provides a portable light emitting device suitable for wide range of applications including dental and industrial photocuring and medical photodynamic therapy.

The device according to the present invention features a light source comprising a semiconductor or solid state light emitting array.

The device according to the present invention also features a pulse circuit for driving the semiconductor emitter array. The pulse circuit can be controlled to provide a range of light dosage outputs. Because the pulse circuit turns the emitter array on for short bursts, overheating of the light emitter array can be controlled.

In a first aspect, the present invention provides a handheld portable light emitting device comprising: (a) a portable housing having a front end and rear end; (b) light emitting semiconducting means having a matrix of a plurality of light emitting diode means mounted at said front end, said light emitting diode means being operative to emit light energy suitable for initiating a photo-reaction; (c) power means coupled to said semiconducting means and operative to provide the electrical power for energizing said plurality of light emitting diode means to emit said light energy; (d) control means connected to said semiconducting means and said power means, and operative to vary the level of said light energy; (e) mounting means provided at said front end of said housing; and (f) an optical assembly mounted to said mounting means, said optical assembly being operative to direct said light energy generated from said light emitting diode means to a photo-reaction location disposed adjacent to said optical assembly.

In a second aspect, the present invention provides a handheld portable photocuring device comprising: (a) a portable housing having a front end and rear end; (b) light emitting semiconducting means having a matrix of a plurality of light emitting diode means mounted at said front end, said light emitting diode means being operative to emit in combination a light energy suitable for photocuring; (c) power means coupled to said semiconducting means and operative to provide the electrical power for energizing said plurality of light emitting diode means to emit in combination said light energy; (d) control means connected to said semiconducting means and said power means, and operative to vary the level of said light energy; (e) mounting means provided at said front end of said housing; and (f) a tubular light guide member mounted to said mounting means, said light guide member being operative to direct said light energy generated from said light emitting diode means to a photocuring location disposed adjacent to a distal free end of said light guide member.

BRIEF DESCRIPTION OF THE DRAWINGS

For a better understanding of the present invention, and to show more clearly how it may be carried into effect, reference will now be made, by way of example, to preferred embodiments of the present invention shown in the accompanying drawings in which:

FIG. 1 shows in diagrammatic form a portable light-emitting device according to the present invention;

FIG. 2 is a block diagram showing another implementation for the system shown in FIG. 1;

DETAILED DESCRIPTION OF THE PREFERRED EMBODIMENTS

Figure 3:
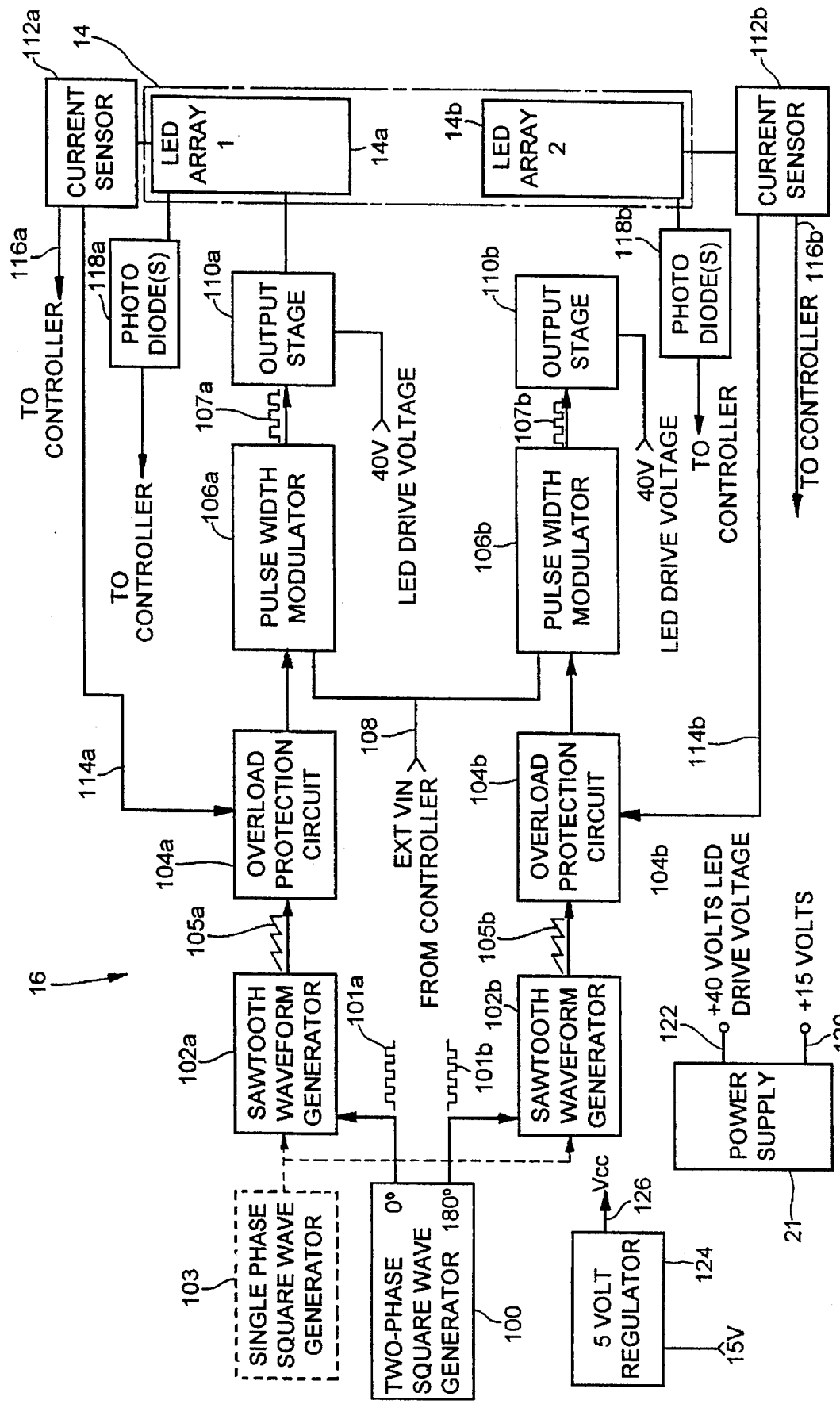
FIG. 3 is a block diagram showing the pulse circuit for driving the LED array.

Reference is first to FIG. 1 which shows a portable light emitting device according to the present invention and denoted generally by reference 10. As shown in FIG. 1, the portable device 10 comprises an enclosure 12, a light source 14, a pulse driver circuit 16, an optical assembly 18 and a power supply 20.

The enclosure 12 provides a compartment or housing for the light source 14, the driver circuit 16 and other components as will be described in more detail below. Since the enclosure 12 also functions as a "handpiece" for the device 10, preferably, the enclosure 12 has an ergonomic shape that fits the palm. The enclosure 12 can be manufactured from a suitable plastic as will be within the understanding of one skilled in the art.

As will be described below, the portable photocuring device 10 according to the invention can be implemented as a fully independent unit which is battery-powered or as a unit which is coupled to an instrument control panel which provides electrical power to the device. The instrument control panel can also provide control signals and cooling as will be described below. For the purposes of this description, the device will be described for use with a dental instrument console as will be understood by those skilled in the art.

The power supply 20 can comprise a power line feed which is coupled to a line power supply 21 as shown in FIG. 2. The power supply 20 can also comprise a local battery power supply shown in broken outline and denoted by reference 21' as shown in FIG. 1. Preferably, the battery supply 21' is rechargeable. A self-contained battery-powered device 10 allows for greater manouverability which is desirable for certain applications.

According to the invention, the light source 14 comprises an array of semiconductor light emitting diodes ("LED") 22 which can include laser diodes. In addition, the LED's 22 forming the array 14 can have various spectral output characteristics, for example, the array 14 can comprise a mix of red and blue LED's, and the spectral characteristics would depend on the application. The light emitting diodes (or LED's) 22 are mounted on a substrate 24, for example a ceramic substrate. As shown in FIG. 1, a heat sink 26 attaches to the back of the substrate 24. The purpose of the heat sink 26 is dissipate heat which is produced as a by-product by the LED's 22. The heat sink 26 draws and dissipates the heat from the substrate 24 and LED array 14. By including the heat sink 26, the LED array 14 can be operated at higher output levels, thereby making the photocuring device 10 suitable for applications requiring high output levels, for example the photocurable materials typically used in dental applications require up to 400 mW/cm$^2$. The portable photocuring device 10 according to the invention is also suitable for medical applications such as photodynamic therapy, which typically requires a light output level in the 100 mW/cm$^2$ range.

The portable photocuring device 10 according to the present invention is suitable for a range of applications in both medical and industrial fields. For example, in a dental application, the LED array 14 can comprise "blue" LED's with a spectral emission in the 470 nanometer range which is suitable for photocuring the dental materials most commonly used. In a dental application, the blue light acts as a photo-initiator which produces a free-radical in the photo-sensitive material. In a medical application, for example photodynamic therapy, the LED array 14 preferably produces a "RED" light in range 600 to 700 nanometers. Because the colour blue is readily absorbed by the skin, the colour red is preferable to provide greater depth of penetration into the skin. By way of background, in photodynamic therapy, the light beam penetrates the skin to produce a "singlet oxygen mechanism" which oxidizes target cells, e.g. cancer cells. Collectively, these types of reactions will be termed a photo-reaction.

To augment the operation of the heat sink 26, the portable photocuring device 10 can include a fan 27. The fan 27 is sized to fit inside the housing 12 and run from the power feed 20. The enclosure 12 includes one or more exhaust ports 28 for the exhaust air from the fan 27. In addition, the enclosure 12 includes an input port 30 to allow the circulation of fresh air. The input port 30 can also be coupled to a compressed air flow 32 which is supplied by the dental console. It will be appreciated that the compressed air flow 32 can eliminate the need for the fan 27.

As shown in FIG. 1, the optical assembly 18 comprises a known fiber optic taper 34. The fiber optic taper 34 serves to condense the light output from the LED array 14 into a condensed beam 36. A condensed beam 36 is desirable for most photocuring applications. The optical assembly 18 can also include a known fiber optic light guide 38 which is coupled to the output end of the fiber optic taper 34. The fiber optic light guide 38 further collimates and focuses the beam 36. In addition, various size, e.g. diameter and length, light guides 38 can be used to improve accessibility in a dental patient's mouth for example. The optical assembly 18 (i.e. fiber optic taper 34 and fiber optic light guide 38) can also be replaced by a transparent optical cap 136 (FIG. 7) which is mounted to the front of the enclosure 12 to gather and collimate the light energy produced by the array 14. The optical cap 136 (FIG. 7) also protects the LED array 14 from contamination. The cap 136 (FIG. 7) can be provided with mounting means (not shown) for attaching the fiber optic light guide 38. A suitable optical cap 136 is the TIR Lens which is available from TIR Technologies Inc. of Costa Mesa, Calif. The description of the TIR type lens in U.S. Pat. No. 4,337,759 is incorporated herein by this reference.

Figure 6:
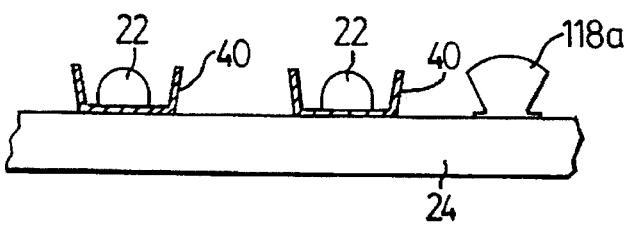
FIG. 6 shows the LED array for the device of FIG. 1 in more detail.

The output from the LED array 14 can also be directed at the source end by including a reflector 40 for each LED 22 mounted on the substrate 24 as shown in FIG. 6. The reflector 40 confines the initially omnidirectional output from the LED 22 into a directed beam. The fiber optic taper 34 then further condenses the output from the LED's 22 comprising the array 14.

Referring back to FIG. 1, the portable photocuring device 10 also includes a switch 42. The switch 42 allows an operator, e.g. dental assistant, to turn on the device 10. The device 10 includes a dial 44 for setting the output power level for the LED array 14. As shown in FIG. 1, the power level dial 44 can be located on the device 10. The device 10 can also include an output display 46. The output display 46 can comprise one or more LED's (not shown) or a LCD panel (not shown). The output display 46 is controlled by a control circuit 48. The control circuit 48 preferably comprises a suitably programmed microprocessor or microcontroller. The control circuit 48 includes an input for receiving signals from the switch 42, an input for receiving signals, e.g. power level settings, from the power level dial 44 and an output for controlling the pulse drive circuit 16. As will be described below, the control circuit 48 can also include an input for monitoring the output level of the LED array 14 and another input for monitoring the drive current level in the LED array 22. The control circuit 48 receives power from the external power feed 21 (or from the internal battery power supply 21').

For the portable photocuring device 10 shown in FIG. 1, the control circuit 48, the array driver 16, the power level dial 44 and the output display 46 are all mounted in the housing 12 which fits into the palm of the operator. The photocuring device 10 can also be implemented as shown in FIG. 2. For the embodiment shown in FIG. 2, the control circuit 48', the LED driver 16', the power level dial 44' and the output display 46' are remote from the housing 12, and provided from a stand-alone console 50 or integrated with a dental console for example. The array driver 16' and control circuit 48' are coupled to the LED array 14 and switch 42 in the housing 12 through wires 52 which are run in a cable for the power supply 21. The embodiment shown in FIG. 2 is typically used where a smaller and lighter handpiece 12 is desired, or where it is desired to integrate the photocuring device 10 with an instrument console such as found in a dental office.

Reference is next made to FIG. 3 which shows the circuit for the LED array driver 16 in block diagram form. According to the invention, the LED array driver 16 comprises a circuit which produces adjustable pulse signals for driving the LED array 14. By providing a pulsed output to the LED array 14 higher output levels can be achieved without generating excess heat. In addition, a pulse drive circuit is more efficient for power consumption and less heat is produced as a by-product.

The output from the pulse drive circuit 16 is varied by adjusting the duty-cycle of the pulses produced in response to the power level dial 44 for example. As shown in FIG. 3, the LED array 14 is divided into two sub-arrays denoted by 14a and 14b respectively. The pulse drive circuit 16 comprises two identical circuits, one for driving each sub-array 14a, 14b. This implementation provides a degree of redundancy and allows the circuit 16 to be divided among a number of printed circuit boards which provides advantages for manufacturing.

As shown in FIG. 3, the drive circuit 16 comprises a two-phase square-wave generator 100 which produces a first square-wave output 101a and a second square-wave output 101b with a fixed frequency $f_c$. The second square-wave 101b is 180 degrees out of phase with the first square-wave 101a. However, the drive circuit 16 can be implemented with a single-phase square-wave generator 103 as shown in broken outline.

The outputs 101a, 101b feed respective sawtooth waveform generators 102a, 102b. The sawtooth waveform generator 102a uses a constant current source and the output 101a from the square-wave generator 100 to produce a sawtooth waveform output 105a. Similarly, the other sawtooth waveform generator 102b uses the 180 degree out-of-phase square waveform 101b to produce a corresponding sawtooth waveform output. When the drive circuit 16 is implemented with the single-phase square-wave generator 103, the sawtooth waveform generators 102a, 102b produce sawtooth waveforms 105a, 105b respectively. The sawtooth waveforms 105a, 105b are fed through overload protection circuits 104a, 104b into respective pulse width modulators 106a, 106b. The pulse width modulators 106a, 106b produce respective output pulse signals 107a, 107b. Each of the output pulse signals 107a, 107b has a duty cycle which is proportional to the instantaneous value of a control voltage EXT $V_{IN}$ provided at control input 108. The output pulse signals 107a, 107b provide the control signals for the respective output stages 110a, 110b which drive the LED array 14. The details of the circuit 16 are described in more detail below with respect to FIG. 4.

The circuit 16 also includes a protection feature for detecting overload and fault conditions in the LED array 14. As shown in FIG. 3, the circuit 16 includes a current sensor 112a coupled to the sub-array 14a and another current sensor 112b coupled to the other sub-array 14b. The current sensor 112a (and 112b) has a sensor output 114a for the overload protection circuit 104a. The overload protection circuit 104a uses the sensor output 114a to monitor overload conditions, for example, a high current flowing through the LED array 14a, and in response, shuts down the pulse width modulator 106a to avoid damaging the LED array 14a. As shown in FIG. 3, the current sensor 112a can also include an output 116a to the control circuit 48. If the output 116a is analog, the control circuit 48 would include an analog-to-digital converter (not shown) for digitizing the sensor signal for processing by the microcontroller. The control circuit 48 can be programmed to reduce the power output of the pulse width modulator 106a as the current flowing in the LED array 14a exceeds a predetermined threshold or value(s). The control circuit 48 can also use this information to activate a warning, for example, on the output display 46, if an overload condition has been reached.

Referring still to FIG. 3, each LED array 14a, 14b can include one or more photodiodes 118a, 118b. Each of the photodiodes 118a, 118b provide an output to the control circuit 48 for monitoring the light output level of each array 14a, 14b. The control circuit 48 can use this information to monitor degradation or failure in the LED array 14a, 14b and in response activate the display 46. In addition, the control circuit 48 can provide a closed loop control system for controlling the intensity and/or output of the LED array 14. In one embodiment, one or more photodiodes 118a are mounted on the substrate 24 with the LED elements 22 as shown in FIG. 6. The control circuit 48 uses the output from the photodiode 118a to calculate the power output of the LED array 14a. If the calculated power output matches the desired level, e.g. as set by the user on the power dial 44, then the control circuit 48 can merely update the display 46. If the calculated power output is below the desired level, then the control circuit 48 can increase the power output through the EXT $V_{IN}$ control line 108 (as described above). The control circuit 48 can also activate the display 46 to indicate low light output or battery power states. Conversely, if the calculated power output exceeds the desired level or maximum allowable level, then the control circuit 48 can decrease the power output through the control input line 108. This function can be implemented in conjunction with the overload protection operation described above.

As shown in FIG. 3, the power supply 21 provides a 15 VDC rail 120 and a 40 VDC rail 122. The 15 VDC rail 120 supplies a voltage regulator 124 which produces a 5 VDC output 126 for powering the circuit 16. The 15 VDC rail 120 also powers other elements in the circuit 16 such as the opto-isolators. The 40 VDC rail 122 is coupled to the output stages 110a, 110b and provides the drive voltage for the LED arrays 14a, 14b. It will be appreciated that for the battery-powered version of the invention 10, the power rail 122 for driving the LED arrays 14a, 14b would be selected to provide both optimal output and power consumption.

Figure 4:
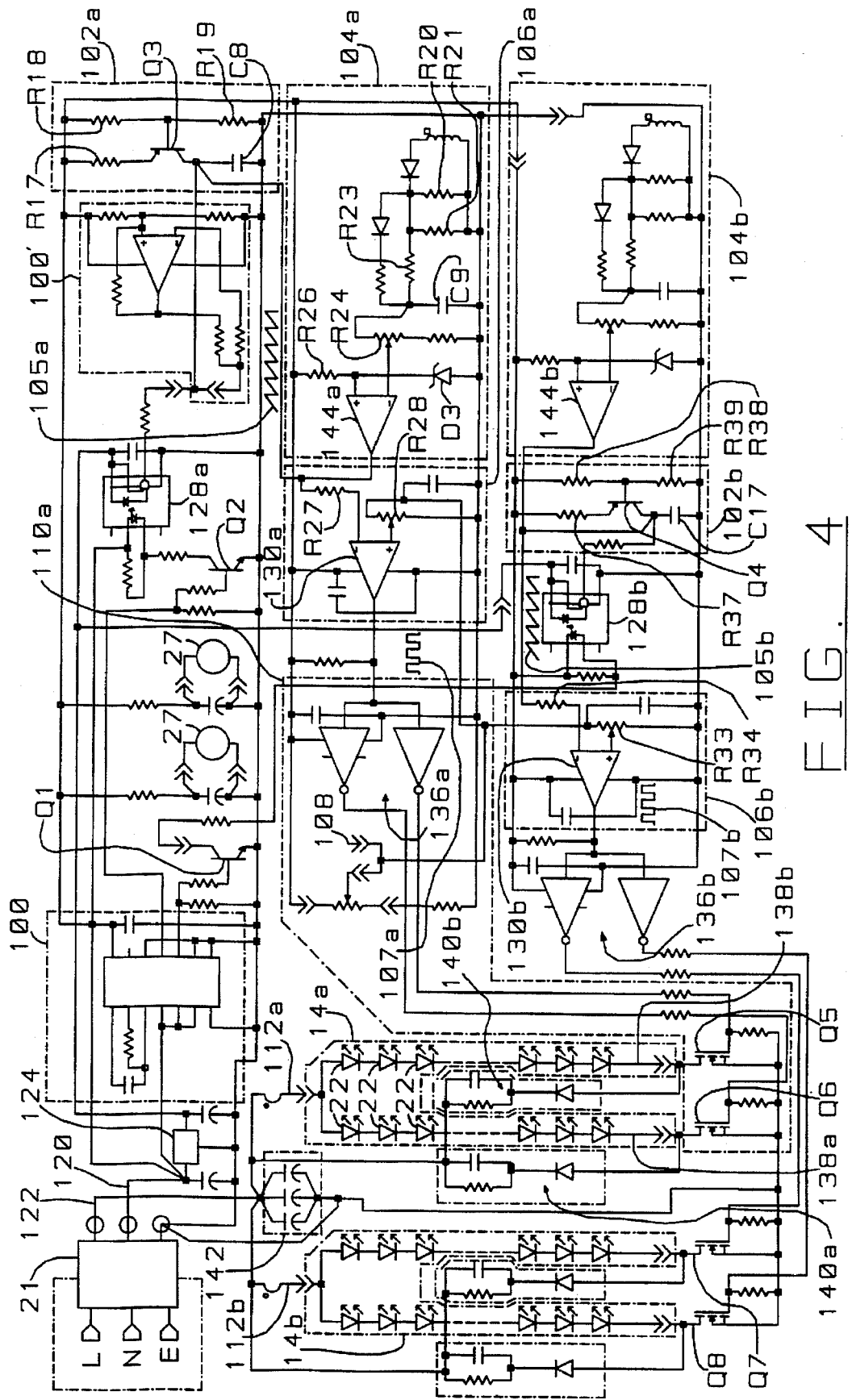
FIG. 4 is a schematic diagram showing in more detail the pulse circuit of FIG. 3.

Reference is next made to FIG. 4 which is a schematic diagram of one embodiment of the circuit 16. In FIGS. 3 and 4, the same reference numbers indicate like components and elements.

As shown in FIG. 4, the power supply 21 comprises an AC-DC dual output supply which supplies 15 VDC 120 and 40 VDC 122. The two-phase square-wave generator 100 comprises an astable multivibrator, such as the CD4047 available from National Semiconductor. Preferably, the output waveforms 101a, 101b produced by the generator 100 have a frequency $f_c$ which is approximately 30 kilohertz above the human audible range. The outputs 101a, 101b from the square-wave generator 100 are coupled to the sawtooth waveform generators 102a, 102b through respective buffer transistors $Q_1$, $Q_2$ to optical isolators 128a, 128b. The optical isolators 128a, 128b provide good isolation between the square wave generator 100 and the sawtooth waveform generator 102a.

In another embodiment, the dual-phase square wave generator 100 can be replaced by a single phase oscillator 100' (denoted as 103 in FIG. 3) shown in broken outline. In this embodiment, a single square wave output drives both sawtooth waveform generators 102a, 102b. This implementation is desirable where a single printed circuit board is used for the circuit 16.

The sawtooth waveform generators 102a, 102b convert the square wave output 101a, 101b into respective sawtooth waveforms 105a, 105b. As shown in FIG. 4, the sawtooth generators 102a, 102b can be implemented as comprising a transistor $Q_3$, $Q_4$, resistors $R_{17}$, $R_{18}$, $R_{19}$ and $R_{37}$, $R_{38}$, $R_{39}$ and capacitors $C_8$, $C_{17}$. The transistors $Q_3$, $Q_4$ together with the resistors $R_{17}$, $R_{18}$, $R_{19}$ and $R_{37}$, $R_{38}$, $R_{39}$ comprise constant current sources which charge the respective capacitors $C_8$, $C_{17}$. The output 105a, 105b from each sawtooth generator 102a, 102b provides one of the inputs to the pulse width modulators 106a, 106b.

As shown in FIG. 4, each of the pulse width modulators 106a, 106b comprises a respective comparator 130a, 130b. The non-inverting input of each comparator 130a, 130b is coupled to the control input 108 through respective potentiometers $R_{28}$, $R_{33}$ and receives the voltage EXT $V_{IN}$ which is generated by the control circuit 48. The potentiometers $R_{28}$, $R_{33}$ are for calibration purposes as will be understood by those skilled in the art. The inverting input of each comparator 130a, 130b is coupled to the output of the respective sawtooth generator 102a, 102b through respective resistors $R_{27}$, $R_{34}$.

Figure 5:
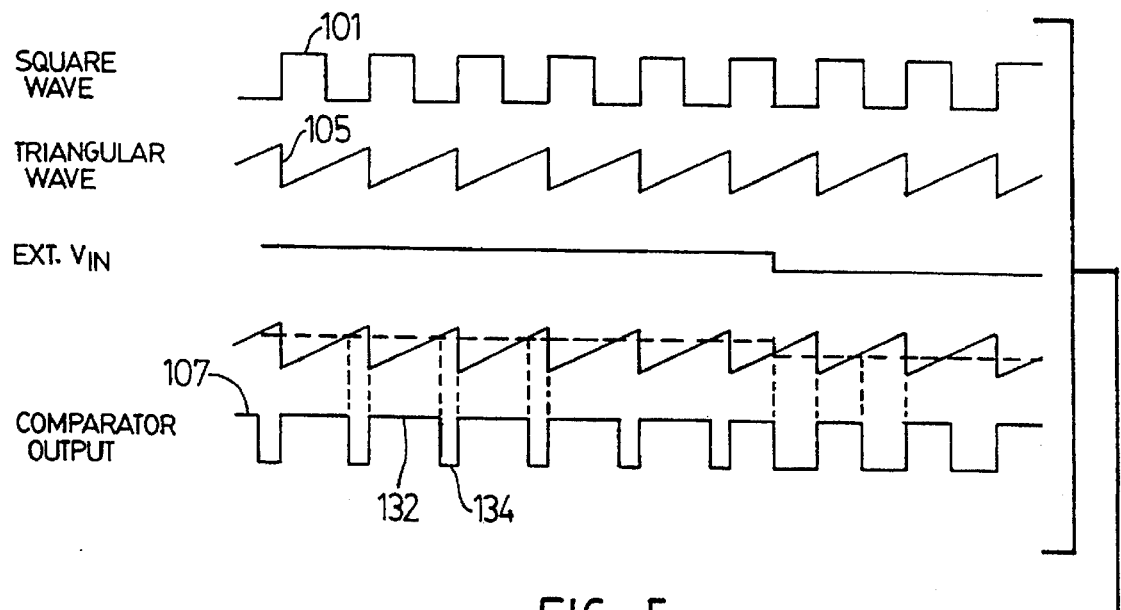
FIG. 5 is a waveform diagram showing the relationship between the output(s) from the pulse circuit and the control voltage EXT $V_{in}$.

In operation, the pulse width modulators 106a, 106b produce a square wave output 107a, 107b having a duty cycle which is proportional to the value of the signal EXT $V_{IN}$ on the input 108. The signal EXT $V_{IN}$ is applied to the non-inverting inputs of the two comparators 130a, 130b which operate at the fixed frequency $f_c$ corresponding to the frequency of the sawtooth waveforms 105a, 105b. The comparators 130a, 130b "compare" the value of the control signal EXT $V_{IN}$ to the instantaneous amplitude of the sawtooth waveforms 105a, 105b. When the value of the signal EXT $V_{IN}$ exceeds the instantaneous amplitude of the sawtooth waveform 105, the output 107a, 107b of the comparator 130a, 130b will go high as indicated by reference 132 in FIG. 5, when the single phase oscillator 100' is used. The output 107a, 107b produced by the comparator 130a, 130b remains high until the instantaneous amplitude of the sawtooth waveform 105a, 105b exceeds the signal EXT $V_{IN}$. When the instantaneous amplitude of the sawtooth waveform 105a, 105b exceeds the signal EXT $V_{IN}$, the output 107a, 107b of the comparator 130a, 130b goes low as indicated by reference 134 in FIG. 5. As can be seen in FIG. 5, the output waveforms 107a, 107b produced by the pulse width modulators 106a, 106b have a duty cycle which is proportional to the value of the signal EXT $V_{IN}$.

Referring again to FIG. 4, the output 107a, 107b from the pulse width modulators 106a, 106b provides a signal for controlling the output drive stage 110a, 110b. The output drive stage 110a, 110b supplies the 40 VDC drive voltage to the LED arrays 14a, 14b. As shown in FIG. 4, each output drive stage 110a, 110b comprises a pair of MOSFET transistors $Q_5$, $Q_6$ and $Q_7$, $Q_8$. Each of the MOSFET pairs $Q_5$, $Q_6$ and $Q_7$, $Q_8$ is coupled to the respective output of the comparator 130a, 130b through a pair of high speed inverting buffers 136a, 136b. The output of the comparator 130a is coupled to the input of both invertors comprising the buffer 136a. The output of one invertor is coupled to the gate (i.e. control input) of the first MOSFET $Q_5$ and the output of other invertor is coupled to the gate of the second MOSFET $Q_6$.

The LED array 14a shown in FIG. 4 has two columns 138a, 138b comprising a series of LED elements 22. It will be appreciated that the array 14a can have more than two columns and one of the determining factors will be the desired light energy output since the number of columns is proportional to the light energy produced by the array 14.

As shown in FIG. 4, the first column 138a is coupled to the drain of the MOSFET $Q_5$ which sinks the current that flows from the 40 VDC rail 122 through the first column 138a. Similarly, the second column 138b is coupled to the drain of the second MOSFET $Q_6$ which sinks the current drawn from the 40 VDC rail 122 and through the second column 138b. Each column 138a, 138b includes a resistor/capacitor network 140a, 140b to protect against excessive flyback voltages produced by parasitic inductance within each array 14a, 14b. The parasitic inductance arises from the component leads and trace layout on the printed circuit board as will be within the understanding of those skilled in the art.

It will be understood that there may be applications where it is desirable to have different colour LED's 22 in the array 14, for example a combination of red and blue LED's. This can be implemented, for example, by using the first column 138a for red LED's and the second column 138b for blue LED's.

The circuit 16 also includes a series of capacitors indicated by reference 142. The capacitors 142 are coupled to the 40 VDC rail 122 and the input to the columns 138a, 138b. The function of the capacitors 142 is to provide the high peak currents needed to drive the columns 138a, 138b. It is desirable to include the capacitors 142 if the power supply 21 is remote from the LED array 14. Preferably, the capacitors 142 have a value of 1000 microfarads or more each.

The current sensor 112a, 112b as shown in FIG. 4 comprises a known current sensing transformer. One winding of the current sensing transformer 112a is electrically coupled to the LED array 14a and the other winding is coupled to a pair of sensing resistors $R_{20}$, $R_{21}$ in the overload protection circuit 104a as shown in FIG. 4. The first winding of the transformer 112a carries all of the current to the LED array 14a and induces a current in the second winding of the transformer 112a which is proportional to the current flowing in the array 14a. The sensing resistors $R_{20}$, $R_{21}$ convert the current induced in the second winding of the transformer into a voltage signal which is applied to the inverting input of a comparator 144a. The non-inverting input of the comparator 144a is coupled to a threshold voltage level produced by a resistor $R_{26}$ and a zener diode $D_3$. The output of the comparator 144a is coupled to the output of the sawtooth generator 102a and the inverting input of the comparator 130a forming the pulse width modulator 106a. If the voltage signal derived from the current sensing transformer 112a exceeds the threshold voltage level, the output of the comparator 144a goes low and clamps the output from the sawtooth generator 102b thereby shutting down the pulse width modulator 106a. The resistor $R_{24}$ provides a means for calibration while resistor $R_{23}$ and capacitor $C_9$ function as a signal conditioner. The operation of the second overload protection circuit 104b is the same as described above.

Figure 7:
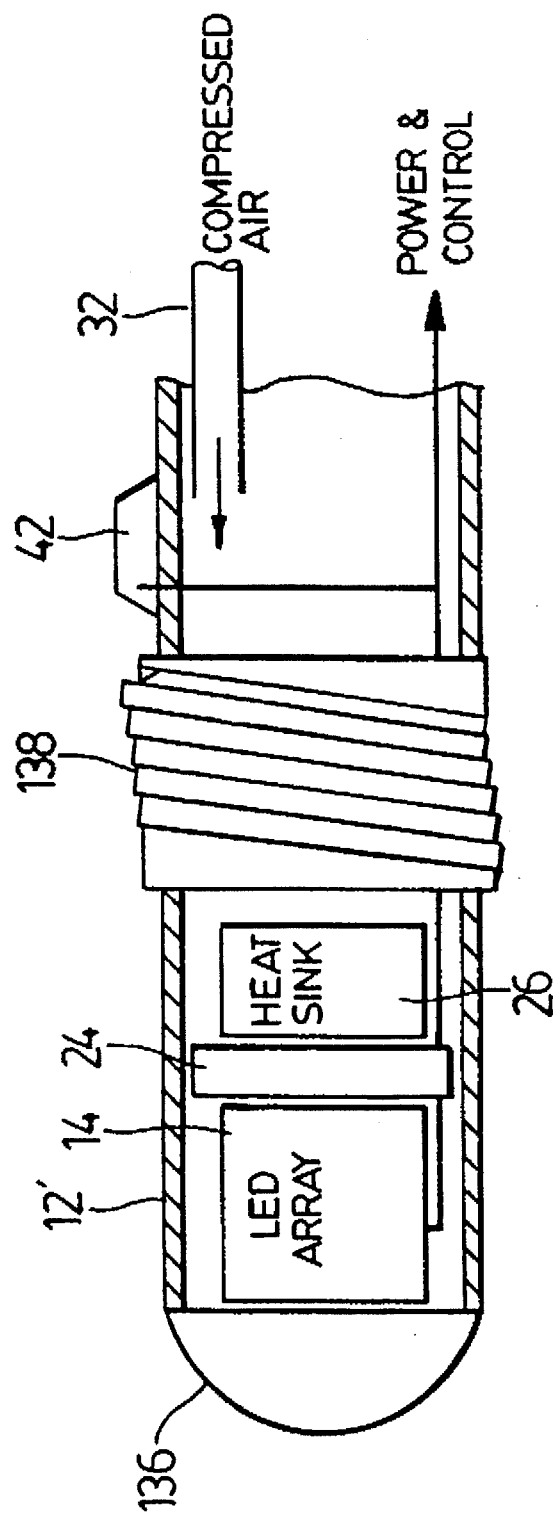
FIG. 7 shows in diagrammatic form another embodiment of a portable device according to the present invention.

In another embodiment of the present invention, the enclosure for the handheld unit 10' is made from an optically clear protective sheath 12' as shown in FIG. 7. The sheath 12' is manufactured from material which can be autoclaved thereby making the handheld unit 10 suitable for sterile medical applications. The sheath 12' is removable for the autoclaving procedure. In another variation, the sheath 12' can be made from a sterile material which is only intended for a single use and then disposal.

For this embodiment of the invention, it is preferable to implement the components as shown in FIG. 2 where the sheath 12' houses the LED array 14 and the heat sink 26 and includes the switch 42. The LED array 14 and switch 42 are coupled to the console through wires 52. If the console includes a compressed air supply 32 this can be used to cool the unit 10' through a tube or pipe (not shown). If the compressed air supply 32 is not available a small fan 27 can be installed inside the sheath 12' as described above for the embodiment of the invention shown in FIG. 1.

As shown in FIG. 7, the optical assembly 18 (i.e. optic taper 34 and light guide 38) can be replaced by an optical cap 136. The cap 136 comprises an optical element, such as the TIR Lens described above, which collimates the light emitting from the LED array 14. The enclosure 12' can also include a bendable elbow 138 which allows the cap 136 and light beam to be oriented in an optimal position or angle for photocuring or phototherapy. Preferably, the elbow 138 comprises a flexible sheath with "memory" that can be bent to a shape so that the device 10 comfortably fits the palm of the dentist or doctor and orients the optical cap 136 at a desired angle. The elbow 138 can also be replaced by a pre-formed joint which fixes the angle of the optical cap 136.

The present invention may be embodied in other specific forms without departing from the spirit or essential characteristics thereof. The presently disclosed embodiments are therefore to be considered in all respects as illustrative and not restrictive, the scope of the invention being indicated by the appended claims rather than the foregoing description, and all changes which come within the meaning and range of equivalency of the claims are therefore intended to be embraced therein.

We claim:

1. A hand-held portable light emitting device comprising:
    (a) a portable housing having a front end and rear end;
    (b) light emitting semiconducting means having a matrix of a plurality of light emitting diode means mounted at said front end, said light emitting diode means being operative to emit light energy, suitable for initiating a photo-reaction;
    (c) power means coupled to said semiconducting means and operative to provide the electrical power for energizing said plurality of light emitting diode means to emit said light energy;
    (d) control means connected to said semiconducting means and said power means, and operative to vary a level of said light energy;
    (e) mounting means provided at said front end of said housing;
    (f) an optical assembly mounted to said mounting means, said optical assembly being operative to direct said light energy generated from said light emitting diode means to a photoreaction location disposed adjacent to said optical assembly;
    (g) wherein said control means comprises drive means for driving said light emitting semiconductor means and a controller for controlling said drive means;
    (h) wherein said drive means includes pulse means for pulsing said light emitting semiconductor means to emit energy suitable for photocuring or phototherapy; and
    (i) wherein said pulse means comprises pulse width modulation means having an oscillator for producing a square-wave output, a sawtooth waveform generator for producing a sawtooth waveform from said square-wave output, and a pulse width modulator for producing an output control signal having a duty cycle and said duty cycle being variable in response to a control input signal generated by said controller and said drive means being responsive to said output control signal for pulsing said light emitting semiconductor means.

2. The hand-held portable device as claimed in claim 1, wherein said optical assembly comprises a tubular light guide member.

3. The hand-held portable device as claimed in claim 1 or 2, wherein said power means comprises a battery disposed in said housing.

4. The hand-held portable device as claimed in claim 1 or 2, wherein said power means comprises an AC power supply.

5. The hand-held portable device as claimed in claim 1 further including cooling means for cooling said light emitting semiconductor means.

6. The hand-held portable device as claimed in claim 5, wherein said cooling means comprises a heat sink thermally coupled to said light emitting semiconductor means for dissipating heat generated in said light emitting semiconductor means.

7. The hand-held portable device as claimed in claim 6, wherein said cooling means includes a fan mounted in said housing for exhausting heat generated in said light emitting semiconductor means through one or more exhaust ports in said housing.

8. The hand-held portable device as claimed in claim 5, wherein said cooling means includes an input port for receiving an external air supply for cooling said light emitting semiconductor means.

9. The hand-held portable device as claimed in claim 1, wherein said portable housing is manufactured from a material suitable for autoclaving.

10. The hand-held portable device as claimed in claim 1, wherein said portable housing includes a removable sheath manufactured from a sterile material.

11. The hand-held portable device as claimed in claim 1, wherein a plurality of said light emitting diode means include means for collimating said emitted light energy.

12. The hand-held portable device as claimed in claim 1, further including optical collimating means mounted between said light emitting semiconducting means and said optical member for collimating and coupling said light energy for said optical member.

13. The hand-held portable device as claimed in claim 12, wherein said optical collimating means comprises a fiber optic taper.

14. The hand-held portable device as claimed in claim 1, wherein said light emitting semiconductor means is capable of emitting light energy having a level of at least 470 nanometers.

15. The hand-held portable device as claimed in claim 1, wherein said light emitting semiconductor means is capable of emitting light energy having a level of at least 660 nanometers.

16. The hand-held portable device as claimed in claim 1, wherein said drive means includes charge storage means for storing drive current for pulsing said light emitting semiconductor means.

17. The hand-held portable device as claimed in claim 16, wherein charge storage means comprise a bank of capacitors.

18. The hand-held portable device as claimed in claim 1, further including a transparent cap member mounted at said front end and covering over said light emitting diode means.

19. A hand-held portable light emitting device comprising:

(a) a portable housing having a front end and rear end;
(b) light emitting semiconducting means having a matrix of a plurality of light emitting diode means mounted at said front end, said light emitting diode means being operative to emit light energy suitable for initiating a photo-reaction;
(c) power means coupled to said semiconducting means and operative to provide the electrical power for energizing said plurality of light emitting diode means to emit said light energy;
(d) control means connected to said semiconducting means and said power means, and operative to vary a level of said light energy;
(e) mounting means provided at said front end of said housing;
(f) an optical assembly mounted to said mounting means, said optical assembly being operative to direct said light energy generated from said light emitting diode means to a photoreaction location disposed adjacent to said optical assembly; and
(g) wherein said power means includes overload sensing means coupled to said light emitting semiconductor means for sensing an overload condition in said light emitting semiconductor means and producing an overload condition signal.

20. The hand-held portable device as claimed in claim 19, wherein said power means includes overload protection means coupled to said power means for suspending operation of said power means in response to said overload condition signal.

21. The hand-held portable device as claimed in claim 20, wherein said overload sensing means comprises a current sensing transformer coupled to said light emitting semiconductor means and having means for sensing a current flowing in said light emitting semiconductor means.

22. The hand-held portable device as claimed in claim 21, wherein said overload protection means comprises a clamping circuit coupled to said power means and having means responsive to said overload condition signal for clamping operation of said power means.

23. A hand-held portable light emitting device comprising:

(a) a portable housing having a front end and rear end;
(b) light emitting semiconducting means having a matrix of a plurality of light emitting diode means mounted at said front end, said light emitting diode means being operative to emit light energy suitable for initiating a photo-reaction;
(c) power means coupled to Said semiconducting means and operative to provide the electrical power for energizing said plurality of light emitting diode means to emit said light energy;
(d) control means connected to said semiconducting means and said power means, and operative to vary a level of said light energy:
(e) mounting means provided at said front end of said housing;
(f) an optical assembly mounted to said mounting means, said optical assembly being operative to direct said light energy generated from Said light emitting diode means to a photoreaction location disposed adjacent to said optical assembly;
(g) wherein said control means comprises drive means for driving said light emitting semiconductor means and a controller for controlling said drive means;
(h) wherein said drive means includes pulse means for pulsing said light emitting semiconductor means to emit energy suitable for photocuring or phototherapy; and
(i) wherein said pulse means includes overload sensing means coupled to said light emitting semiconductor means for sensing an overload condition in said light emitting semiconductor means and producing an overload condition signal.

24. The hand-held portable as claimed in claim 23, wherein said control means includes overload protection means coupled to said drive means for suspending operation of said pulse means in response to said overload condition signal.

25. The hand-held portable device as claimed in claim 24, wherein said overload sensing means comprises a current sensing transformer coupled to said light emitting semiconductor means and having means for sensing a current flowing in said light emitting semiconductor means.

26. The hand-held portable device as claimed in claim 25, wherein said overload protection means comprises a clamping circuit coupled to said pulse means and having means responsive to said overload condition signal for clamping operation of said pulse means.

27. A hand-held portable light emitting device comprising:

(a) a portable housing having a front end and rear end;
(b) light emitting semiconducting means having a matrix of a plurality of light emitting diode means mounted at said front end, said light emitting diode means being operative to emit light energy suitable for initiating a photo-reaction;
(c) power means coupled to said semiconducting means and operative to provide the electrical power for energizing said plurality of light emitting diode means to emit said light energy;
(d) control means connected to said semiconducting means and said power means, and operative to vary a level of said light energy;
(e) mounting means provided at said front end of said housing;
(f) an optical assembly mounted to said mounting means, said optical assembly being operative to direct said light energy generated from said light emitting diode means to a photoreaction location disposed adjacent to said optical assembly; and
(g) further including photosensing means for sensing light energy produced by said light emitting semiconductor means and producing a light output signal for said control means.

28. The hand-held portable device as claimed in claim 27, wherein said photosensing means are located proximate said light emitting diode means.

29. The hand-held portable device as claimed in claim 28, wherein said photosensing means comprises a photodiode.

30. The hand-held portable device as claimed in claim 27, wherein said control means includes a suitably programmed microprocessor coupled to said photosensing means to receive light output signals and to output a control signal for controlling said power means.

31. The hand-held portable device as claimed in claim 30, wherein said control means includes input means for setting a desired light energy level and said microprocessor includes means for maintaining said desired light energy level in response to said light output signals.

* * * * *